United States Patent [19]

Revis et al.

[11] Patent Number: 4,826,602

[45] Date of Patent: May 2, 1989

[54] REDUCTION OF TRACE ELEMENTS TO THE ELEMENTAL FORM BY MICROORGANISMS

[75] Inventors: Nathaniel W. Revis, Oak Ridge; Suzanne B. Benson, Kingston; Tanya R. Osborne; Charles T. Hadden, both of Oak Ridge, all of Tenn.

[73] Assignee: Oak Ridge Research Institute, Oak Ridge, Tenn.

[21] Appl. No.: 162,022

[22] Filed: Feb. 29, 1988

Related U.S. Application Data

[60] Division of Ser. No. 34,329, Apr. 3, 1987, Pat. No. 4,728,427, which is a continuation-in-part of Ser. No. 918,768, Oct. 14, 1986, abandoned.

[51] Int. Cl.$^4$ ................................................ C02F 3/34
[52] U.S. Cl. .................................... 210/611; 210/615; 210/914; 435/168; 435/262; 435/874; 435/253.3
[58] Field of Search ................ 210/610, 611, 615–619, 210/622, 912, 913, 914; 435/168, 253, 262, 874

[56] References Cited

U.S. PATENT DOCUMENTS

| | | | |
|---|---|---|---|
| 3,867,255 | 2/1975 | Newell | 426/656 |
| 3,915,853 | 10/1975 | Luck | 210/611 |
| 3,923,597 | 12/1975 | Chakrabarty | 210/611 |
| 3,934,039 | 1/1976 | Cardini | 426/656 |
| 4,159,944 | 7/1979 | Erickson | 210/912 |
| 4,267,049 | 5/1981 | Erickson | 210/912 |
| 4,277,342 | 7/1981 | Hayes | 210/912 |
| 4,342,650 | 8/1982 | Erickson | 210/912 |
| 4,370,233 | 1/1983 | Hayes | 210/912 |
| 4,468,461 | 8/1984 | Bopp | 210/611 |
| 4,504,394 | 3/1985 | Brear | 210/912 |
| 4,519,912 | 5/1985 | Kauffman | 210/912 |
| 4,519,913 | 5/1985 | Baldwin | 210/912 |
| 4,522,723 | 6/1985 | Kauffman | 210/912 |
| 4,530,763 | 7/1985 | Clyde | 210/912 |

FOREIGN PATENT DOCUMENTS

| | | | |
|---|---|---|---|
| 47185 | 1/1972 | Japan | 210/914 |
| 844630 | 7/1981 | U.S.S.R. | 210/611 |
| 916441 | 4/1982 | U.S.S.R. | 210/611 |

*Primary Examiner*—Ernest G. Therkorn
*Attorney, Agent, or Firm*—Bailey & Hardaway

[57] ABSTRACT

A process for reducing the concentration of ionic species of heavy metals in an aqueous waste solution by conversion to a corresponding elemental metal comprises contacting the waste solution containing ionic species of one or more heavy metals with a culture of *Pseudomonas maltiphilia* ATCC 53510 in the presence of an amount of nutrient medium sufficient to satisfy nutritional requirements of cells of the culture of *Pseudomonas maltiphilia* ATCC 53510. When the ionic species is other than $Hg^+$ or $Hg^{++}$, other species of Pseudomonas can be used.

9 Claims, No Drawings

REDUCTION OF TRACE ELEMENTS TO THE ELEMENTAL FORM BY MICROORGANISMS

This application is a division of application Ser. No. 034,329, filed Apr. 3, 1987, now U.S. Pat. No. 4,728,427 which, in turn, is a continuation-in-part of Ser. No. 918,768, filed Oct. 14, 1986, now abandoned.

TECHNICAL FIELD

This invention relates to the use of Pseudomonas organisms to reduce objectionable ionic species of heavy metals in waste waters to the elemental form and to thus reduce the concentration of the heavy metal in the waste water.

BACKGROUND ART

Trace elements are widely used in industry and for medicinal purposes. Platinum, mercury, cadmium and lead are used in the plating industry, for example, to make electrodes for batteries and lamps. Compounds of these metals are used as catalysts for making varnish and paint compositions.

Waste waters from mining and public utilities also contain toxic heavy metals or their compounds. In addition, disposal of radionuclides from aqueous wastes of nuclear power plants is an important problem.

Disposal of wastes from these industries presents an ecological problem, particularly when the heavy metals are in the form of organic compounds or complexes, such as methylated mercury or lead. Organometallic compounds in waste waters are generally considered more objectionable than inorganic metal compounds or elemental metals because consumption of waters, containing organometallic compounds, by humans or domestic animals results in absorption and accumulation of relatively large amounts of heavy metal compounds in the organs of the animals, which consume the water. Organometallic compounds are absorbed from the intestinal tract much more readily than inorganic metal compounds or the free metals themselves. Moreover, organometallic compounds can cross the blood-brain barrier, accumulate in nervous tissue and cause disorders of the nervous system. Therefore, there is considerable interest in processes for removing toxic or objectionable heavy metal species from waste waters.

Summers et al., "Volatilization of Mercuric Chloride by Mercury-Resistant Plasmid-Bearing Strains of *Escherichia coli, Staphylococcus aureus*, and *Pseudomonas aeruginosa*," *J. Bacteriol.*, vol. 113 (1973), pages 1070–1072, have recited that strains PU21/FP, PU21/-Stone and PU21/PS18 of *Pseudomonas aeruginosa* appear to convert mercuric chloride to elemental mercury, or another mercurial composition, which is volatile and soluble in organic solvents.

Chakrabarty et al. (U.S. Pat. No. 3,923,597) have proposed using genetically-engineered Pseudomonas bacteria to concentrate mercury or its compounds from liquid streams.

Walker et al., "Mercury-Resistant Bacteria and Petroleum Degradation," *Appl. Microbiol.*, vol. 27 (1974), pages 285–287 and Kondo et al., "Mercury and Cadmium Resistances Mediated by the Penicillinase Plasmid in *Staphylococcus aureus*," *J. Bacteriol.*, vol. 117 (1974), pages 1–7, recite characteristics of mercury-resistant organisms.

Bopp, in U.S. Pat. No. 4,468,461, has proposed using *Pseudomonas fluorescens* NRRL B-12596 to reduce chromate ions to chromic ions in aqueous solution. The chromic ions are precipitated at about neutral pH.

Kauffman et al. (U.S. Pat. No. 4,519,912) and Bakldwin et al. (U.S. Pat. No. 4,519,913) have proposed removing objectionable water-soluble species from aqueous solutions by treatment with various bacterial organisms. The proposed processes rely upon reduction of the ionic species to a corresponding elemental metal.

It is therefore apparent that removal of objectionable and toxic ionic or organometallic species of heavy metals from waste waters is of continuing importance in recycling of waste waters to provide water supplies, which are safe for drinking or industrial uses.

It is an object of this invention to provide processes by which toxic and objectionable heavy metal species can be removed from waste waters.

DISCLOSURE OF INVENTION

A process for reducing the concentration of ionic species of at least one heavy metal, other than mercury, in an aqueous waste solution by conversion to one or more corresponding elemental metals, comprises contacting the aqueous waste solution containing ionic species of at least one heavy metal with a culture of a Pseudomonas organism in the presence of an amount of nutrient medium, sufficient to satify nutritional requirements of cells of the culture of Pseudomonas.

This invention further relates to a process for reducing the concentration of ionic species of mercury in an aqueous waste solution by conversion to elemental mercury, comprising contacting the aqueous waste solution with a culture of *Pseudomonas maltophila* ATCC 53510, otherwise as above.

In another aspect, this invention relates to a process for reducing the concentration of ionic species of zinc or cadmium in an aqueous waste solution by conversion to elemental zinc or cadmium or by accumualtion in or on cells of microorganisms, by contacting the aqueous waste solution with a culture of Pseudomonas, as above.

In yet another aspect, this invention relates to a biologically pure culture of a strain of *Pseudomanas maltophila*, having the identifying characteristics of *Pseudomonas maltophilia* ATCC 53510. For the practice of this invention, a culture of the microorganism designated *Pseudomonas maltophila* ATCC 53510 has been deposited with the American Type Culture Collection, Bethesda, Md.

In the event that during pendency of this application, the Commissioner of Patents and Trademarks shall determine that some individual is entitled to receive progeny of this strain in accordance with the provisions of 37 C.F.R. 1.14 and 35 U.S.C. 122, the required written authorization will be provided by the assignee of this application.

Upon the issuance of this application as a patent, a culture of this strain can be obtained from the permanent collection of the American Type Culture Collection, Bethesda, Md.

*Pseudomanas maltophila* ATCC 53510 and Pseudomonas species, generally, require a minimal growth medium containing arginine, methionine, glucose, beta-glycerophosphate, alanine, phenylalanine, serine, valine, sodium chloride, potassium chloride, magnesium sulfate and ammonium sulfate. The minimal medium also contains a buffer, preferably 2-amino-2-hydroxymethyl-1,3-propanediol, also known as TRIS buffer.

The minimal medium preferably contains, per liter:

| grams | |
|---|---|
| 5–10 g | TRIS |
| 0.05–0.2 | ammonium sulfate |
| 0.05–0.2 | arginine |
| 0.05–0.2 | methionine |
| 0.5–2 | sodium chloride |
| 0.5–2 | potassium chloride |
| 0.1–0.5 | magnesium sulfate |
| 2.5–10 | glucose |
| 0.5–1 | beta-glycerophosphate |
| 0.1–1 | alanine |
| 0.5–1.5 | phenylalanine |
| 0.15–0.5 | serine |
| 0.05–0.5 | valine | and the pH is adjusted to about 7.2 with 4N hydrochloric acid.

The foregoing minimal medium is that "sufficient to satisfy nutritional requirements of cells of the culture of *Pseudomonas maltophila* ATCC 53510," as used in the specification and claims.

Contemplated equivalents of the minimal medium, providing sufficient nutrients to support the nutritional requirements of cells of the Pseudomonas culture, include, but are not limited to, (a) mineral salts, including sulfates and phosphates; (b) amino acids, including methionine and (c) a carbon source, e.g. g.ucose.

The aqueous waste solutions are contacted with *Pseudomonas maltophilia* ATCC 53510 or an equivalent organism at temperatures ranging from about 5° to about 35° C. However, for optimum culture growth, it is preferred to treat or contact the waste waters with Pseudomonas cultures at higher temperatures, more preferably from about 25° C. to about 35° C.

The pH of the mixture of culture and aqueous waste solution during treatment is preferably near neutrality, that is, pH from about 6 to about 8. When confluent cultures are mixed with aqueous wastes containing trace metal species, normal osmolality should also be maintained.

The process of this invention is utilized for removal of significant amounts of trace metal compounds from waste waters. It is used for reduction of levels as high as about 50 ppm. However, it is preferred to operate the process using feeds containing from a few ppb to about 25 ppm.

The time for contacting the aqueous waste solutions with Pseudomonas organisms is selected to accomplish reduction of the objectionable ionic heavy metal species to the desired extent. The time required can be as little as 5–10 minutes when the aqueous waste is treated with confluent cells. More prolonged treatment times, of the order of 12 hours or more, maya be required when the aqueous waste solutions are being treated with growing cultures of Pseudomonas organisms. It will be understood that one skilled in the art can determine preferred and optimum contact times by routine experimentation.

"Ionic species of heavy metals," as used in the specification and claims, includes both organic and inorganic compounds of heavy metals, in which the metal is bonded by an electrovalent bond to another element or to a carbon-containing radical. Covalently-bonded compounds are also within the scope of this definition. Compounds which can be treated by the process of this invention include, but are not limited to chlorides, bromides, acetates, propionates, naphthenates, benzoates, nitrates, and phenolates of cations such mercury, lead, cadmium, zinc, silver, gold, chromium, platinum, and copper in various positive-valence states. Treatment of selenium-containing compounds, e.g., sodium or potassium selenate, is also included. It will be understood that the process of this invention can also be used to treat organometallic compounds, more particularly, compounds in which the metal-carbon bond is covalent. Exemplary of organometallic compounds which can be treated by the process of this invention are methyl mercury, dimethyl mercury, diphenyl lead, dipropyl cadmium, tetraethyl lead and triethyl tin.

"Elemental metal" means the metal in its zerovalent condition.

Waste waters are preferably contacted with the selected Pseudomonas culture under aerobic conditions. The process of the present invention is accordingly preferably carried out under ambient conditions, without exclusion of air from the container in which the treatment is being done. Most preferably, air is bubbled through the mixture of waste water and culturing during the treatment. A preferred rate of air flow for this type of aeration is 1 ml/min.

In the practice of this invention, mercuric or mercurous ions in waste waters are reduced to metallic mercury by treatment or incubation with *Pseudomonas maltophilia* ATCC 53510. Other metallic species, particularly $Cu^{++}$, $Cr^{+++}$, $Hg^{++}$ or $Pb^{++}$, can be incubated with a variety of Pseudomonas species, preferably *Pseudomonas syringae* or *Pseudomonas denitrificans*. Most preferably, the waste waters containing ionic species of these metals, are contacted with a culture of *Pseudomonas maltophila* ATCC 53510.

It has further been found, in accordance with the practice of this invention, that selected Pseudomonas organisms, particulary *Pseudomonas maltophila* ATCC 53510, can reduce mixtures, containing several of the species $Pb^{++}$, $Au^+$, $Ag^+$, $Cr^{+++}$, $As^{++}$, $SeO_3^=$, $Pt^{++++}$ and $Cu^{++}$ essentially completely to corresponding metals in a reasonable time. Therefore, the method of this invention is useful for reducing the concentrations of mixtures of toxic or obnoxious ionic species in waste waters to corresponding metals and for removing significant amounts of the metals from the waste solutions.

It has also been found that ionic species of zinc and cadmium are partially reduced to corresponding metals by Pseudomonas organisms and that significant accumulation of zinc and cadmium in the organisms of the culture serves to reduce the concentration of these ionic spcies in the waste water. Therefore, despite the way in which treatment of waters, contaminated with $Zn^{++}$ or $Cd^{++}$, operates, the concentration of these ions in the waste solution being treated is nevertheless decreased.

The amount of reduction of varous metallic ions in waste waters was demonstrated by analyzing incubates by sucrose gradient analysis. Metal content of the various sucrose gredients permitted accounting for the disposition of the metallic ions in a sample, following treatment with the active cultures.

Treatment of the mixture of waste water and culture can be done in an essentially liquid medium. That is, when the waste water or aqueous waste solution is relatively free of dispersed particulate matter, the culture is added to the waste water in the form of a broth. Following the recommended incubation or treatment period, the incubate can be filtered and reduced metal species can be recovered from the residue on the filter. Elemental metal can be recovered, for example, by digesting the residue with nitric acid to destroy the cellular structure of the culture and to dissolve the metals entrained with the cells. The resulting nitrate solution is treated in conventional ways to recover corresponding elemental metals.

The waste waters can also be contacted with a supported cultures of Pseudomonas organism. The waste waters can be passed through one or more beds of microorganisms, immobilized on, or adhered to, beads of plastic, alginic acid or the like. Use of a bed of supported organism is preferred, because water treatment can be done continuously, with periodic withdrawal of the beds from service to recover reduced metal species therefrom. When the process is being done using supported microorganisms, it will be understood that materials required for meeting the nutrient requirements of the cells of the culture are added to the feed of aqueous waste. The pH of the feed stream will also be adjusted, as necessary.

In batch processes for treating aqueous waste streams, the concentration of microorganisms will preferably be at least $10^8$ cells/ml of solution, while for continuous processes, the concentration of organimsms will be at least $10^4$ cells/ml of waste solution. More preferably, concentrations of cells for continuous and batch processes will be above $10^{11}$ and $10^7$ cells/ml, respectively. The preferred maximum, concentration of cells during treatment is determined by the rheology of the resulting system. However, in general, the cellular content should not exceed $10^{18}$ and $10^{15}$ cells/ml for batch and continuous processes, respectively.

The process of this invention can be carried out in several stages. When the aqueous feed contains high concentratons of heavy metal species, it is preferred to treat the feeds by several treatment steps, each of which results in reducing the concentration of heavy metal species in the feed.

It has been found that addition of an antibiotic, particularly penicillin, ampicillin or 6-aminopenicillanic acid, improves the process. A preferred level of antibiotic addition is 50 micrograms/ml. The preferred antibiotic is ampicillin.

It is proposed that reduction of metal species by the Pseudomonas culture is accomplished by a reductase enzyme, secreted by the organisms. However, it will be understood that the applicants do not wish to be bound by any proposed theoretical explanations and that the protection being sought is that, set forth in the appended claims.

BEST MODE FOR CARRYING OUT THE INVENTION

In a most preferred embodiment, the process of this invention is carried out under aerobic conditions and air is bubbled through a culture of *Pseudomonas maltophilia* ATCC 53510 and aqueous waste solution. For a continuous process, a concentration of at least $10^4$ cells/ml is preferred. For a batch process, a minimum concentration of $10^8$ cells/ml. is preferred.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, temperatures are set forth uncorrected in degrees Celsius. Unless otherwise indicated, all parts and percentages are by weight.

EXAMPLE 1

Minimal Medium for Pseudomonas

Minimal medium concentrate is prepared by dissolving ingredients, shown in Table 1, in 1000 mL of distilled water. The pH of the solution is adjusted to 7.2 with 4N HCl. The concentrate is sterilized by autoclaving.

Medium is prepared by diluting 100 mL of concentrate with 900 mL of distilled water.

EXAMPLE 2

Reduction of Ionic Heavy Metal Species by Cultures of Pseudomonas

*Pseudomonas maltophila* ATCC 53510 is grown in minimal medium of Example 1, to which is added trace amounts of representative heavy metal cations. The initial cellular concentration is $10^3$ cells/ml of solution. The cultures are incubated at 30° C. for 12 h.

At the end of the incubation period, 2-ml aliquots of incubate are removed, placed on sucrose gradients and centrifuged. Aliquots of the various gradients are removed and analyzed for metal content by atomic absorption.

Each ionic metal species was incubated with a culture of *Pseudomonas maltophila* ATCC 53510.

Results for samples, containing various metals, are shown in Table 2. The figures shown represent the mean ±SD for each series of three experiments.

The procedure used permits separation of medium from cells and heavy metal elements. The density of the heavy metal element is higher than that of a corresponding ionic species. Centrifugation of sugar gradients results in settling of elemental metals to the bottom layer (50% sucrose), and concentration of the cells in the middle layer (20% sucrose) and of ionic species in the top layer (10% sucrose).

TABLE 1

| Concentrate for Minimal Media for Pseudomonas** | |
|---|---|
| | grams |
| TRIS* | 60.5 |
| (NH4)2SO4 | 1 |
| Arginine | 1 |
| Methionine | 1 |
| NaCl | 10 |
| KCl | 10 |
| MgSO4 | 2 |
| Glucose | 50 |
| beta-Glycerophosphate | 6.8 |
| Alanine | 1.8 |
| Phenylalanine | 9 |
| Serine | 2.20 |
| Valine | 1.2 |

*2-Amino-2-hydroxyethyl-1,3-propanediol
**The solutes the concentrate were dissolved in 1000 ml of distilled water and pH as adjusted to 7.2 with 4 N HCl. The concentrate was sterilized by autoclaving. Minimal medium was prepared by diluting 100 ml of the concentrate with 900 ml of distilled water.

TABLE 2

| Distribution of Heavy Metal Species Demonstrated by Sucrose Gradient Analysis-following Reduction with Pseudomonas(a) | | | | |
|---|---|---|---|---|
| | | % Sucrose | | |
| | | 10 (Top)(b) | 20(Middle)(c) | 50 (Bottom)(d) |
| | | [as % of total inorganic ions added/ml of culture] | | |
| Controls(e) | | 89–100 | | |
| PbCl2 | 2 μg/mL | 5 ± 2 | 15 ± 1 | 80 ± 5 |
| AgCl2 | 20 μg/mL | 1 ± 1 | 6 ± 0.5 | 93 ± 6 |
| AuCl2 | 20 μg/mL | 2 ± 0.1 | 5 ± 2 | 93 ± 12 |

TABLE 2-continued

Distribution of Heavy Metal Species Demonstrated by Sucrose Gradient Analysis-following Reduction with Pseudomonas[a]

| | | % Sucrose | | |
|---|---|---|---|---|
| | | 10 (Top)[b] | 20(Middle)[c] | 50 (Bottom)[d] |
| | | [as % of total inorganic ions added/ml of culture] | | |
| HgCl$_2$ | 20 μg/mL | 4 ± 2 | 10 ± 1 | 86 ± 6 |
| Na$_2$SeO$_3$ | 3 μg/mL | 8 ± 4 | 28 ± 4 | 64 ± 15 |
| PtCl$_2$ | 20 μg/mL | 5 ± 1 | 10 ± 3 | 85 ± 9 |
| CuCl$_2$ | 20 μg/mL | 3 ± 2 | 7 ± 6 | 90 ± 4 |
| CdCl$_2$ | 20 μg/mL | 25 ± 5 | 40 ± 1 | 35 ± 13 |
| ZnCl$_2$ | 20 μg/mL | 50 ± 8 | 38 ± 4 | 12 ± 2 |

[a]Results represent mean ± SD
[b]Metal content of medium layer
[c]Metal content of bacterial layer
[d]Elemental metal layer
[e]Samples incubated with metals and without Pseudomonas culture The culture-free samples (controls) have a high concentration (90–100%) of heavy metal ion in the top layer. Many incubated samples, containing active Pseudomonas culture, show high concentrations of elemental metal, as indicated by high metal content in the bottom (50% sucrose) gradient. These results show that Pb++, Ag+, Au+, Hg++, SeO$_3$=, Pt++ and Cu++ are reduced to the greatest extent by *Pseudomonas maltophila* ATCC 53510. Results for the incubation of Cd++ and Zn++ with *Pseudomonas maltophila* ATCC 53510 suggest that concentration of these metals, in some form, in the cellular material, is significant and that some reduction to elemental metal also occurs.

EXAMPLE 3

Extent of Reduction of Ionic Species as a Function of Incubation Time

Cultures are incubated at 30° C. as in Example 2. The initial concentration of *Pseudomonas maltophila* ATCC 53510 is 10$^3$ cells/ml. Aliquots are removed after 4, 8, 12 and 24 h and subjected to sucrose gradient analysis. Aliquots from the 50% sucrose layer are removed and analyzed by atomic absorption spectroscopy for heavy metal content. An alternative analysis of samples is by filtration of an aliquot through a 0.45 micron filter, which is digested in nitric acid to determine metal content.

Results are given in Table 3. The first set of numbers corresponds to mean ± SD for three sugar gradient experiments. the numbers in parentheses correspond to results from filtration studies, also from experiments in triplicate.

These experiments show that increased incubation time is associated with increasing reduction of ionic metallic species to elemental metal. These results further show that, after 12 hours' incubation, most of the readily-reducible metallic species have been reduced. As in Example 2, Cd++ and Zn++ were not as readily reduced. For corresponding culture-free experiments (controls), less than 4% of the ionic species are detected in the 50% sucrose gradient.

TABLE 3

Atomic Absorption and Membrane Filtration Analyses of Extent of Reduction of Heavy Metal Ions by Pseudomonas as a Function of Time[a]

| | | Incubation Time (h) | | | |
|---|---|---|---|---|---|
| | | 4 | 8 | 12 | 24 |
| | | [% of total inorganic ion added/ml of culture] | | | |
| PbCl$_2$ | 2 μg/mL | 40 ± 3 | 60 ± 4 | 75 ± 7 | 79 ± 11 |

TABLE 3-continued

Atomic Absorption and Membrane Filtration Analyses of Extent of Reduction of Heavy Metal Ions by Pseudomonas as a Function of Time[a]

| | | Incubation Time (h) | | | |
|---|---|---|---|---|---|
| | | 4 | 8 | 12 | 24 |
| | | [% of total inorganic ion added/ml of culture] | | | |
| | | (36) | (71) | (70) | (83) |
| AgCl$_2$ | 20 μg/mL | 60 ± 2 | 80 ± 6 | 90 ± 8 | 83 ± 8 |
| | | (51) | (68) | (88) | (87) |
| AuCl$_2$ | 20 μg/mL | 65 ± 4 | 89 ± 9 | 90 ± 8 | 90 ± 9 |
| | | (69) | (74) | (86) | (81) |
| HgCl$_2$ | 20 μg/mL | 50 ± 4 | 60 ± 5 | 80 ± 4 | 85 ± 6 |
| | | (55) | (60) | (73) | (73) |
| Na$_2$SeO$_3$ | 3 μg/mL | 35 ± 1 | 46 ± 5 | 59 ± 10 | 48 ± 4 |
| | | (21) | (38) | (42) | (40) |
| PtCl$_2$ | 20 μg/mL | 20 ± 6 | 60 ± 8 | 79 ± 14 | 89 ± 8 |
| | | (29) | (71) | (70) | (71) |
| CuCl$_2$ | 20 μg/mL | 71 ± 3 | 79 ± 10 | 88 ± 6 | 90 ± 9 |
| | | (55) | (89) | (80) | (83) |
| CdCl$_2$ | 20 μg/mL | 10 ± 2 | 9 ± 3 | 30 ± 9 | 40 ± 8 |
| | | (15) | (25) | (49) | (50) |
| ZnCl$_2$ | 20 μg/mL | 15 ± 8 | 10 ± 4 | 13 ± 7 | 15 ± 3 |
| | | (38) | (29) | (30) | (24) |
| Control[b] | | <4 | <4 | <4 | <4 |

[a]Results are shown as mean ± SD for atomic absorption analysis of 50% sucrose layer (heavy metal element); results in parentheses are from membrane filtration analysis.
[b]No Pseudomonas added.

EXAMPLE 4

Effect of Aeration on Reduction of Ionic Metal Species

Samples containing a mixture of heavy metal ions are incubated with *Pseudomonas maltophilaa* ATCC 53510 (10$^3$ cells/ml) at 30° C. for 12 h. In one series of experiments, air is bubbled through the mixture of culture and sample at a rate of 1 ml./min. In the other series, no air was added, but the cultures were incubated in the ambient atmosphere.

At the end of 12 hrs' incubation, 4-ml aliquots are removed and filtered. The residue on the filter is digested in nitric acid and analyzed by atomic absorption for metal content. Results shown in Table 4 are for experiments in triplicate. The numbers given represent means ±SD.

Controls (culture-free sample) are analyzed by sucrose gradient analysis. The controls have less than 6% of the metal, initially present, in the form of elemental metal in the 50% sucrose layer.

These results show that bubbling air through the cultures and sample improves reduction of ionic species to corresponding metals and that all of the readily-reducible metals in the mixture, Pb++, Ag+, Au+, Hg++, Pt++ and Cu++, are reduced equally well.

EXAMPLE 5

Determination of Optimum Conditions for Reduction

Maximum reduction of ionic species of heavy metal ions is facilitated by using minimal medium, containing TRIS buffer, ammonium sulfate, arginine, methionine, sodium and potassium chlorides, magnesium sulfate, glucose, betaglycerophosphate, alanine, phenylalanine, serine and valine.

For a continuous process, incubation at a level of at 10$^7$ cells/ml is preferred. For a batch process, the culture level is preferably 10$^{11}$ cells/ml.

Bubbling air through the mixture of sample and culture improves the conversion of ionic species to elemental metal.

Addition of an antibiotic, such as ampicillin (50 micrograms/ml) also benefits the process. Contemplated equivalent antibiotics are penicillin and 6-amino-penicillanic acid at levels of 100 micrograms/ml.

TABLE 4

Effect of Aeration on Reduction of Heavy Metal Ions by Pseudomonas[a]

| | | With air bubbling | Without air bubbling |
|---|---|---|---|
| | | [% of total inorganic ion added/mL of culture] | |
| $PbCl_2$ | 2 μg/mL | 93 ± 6 | 70 ± 7 |
| $AgCl_2$ | 20 μg/mL | 98 ± 2 | 90 ± 8 |
| $AuCl_2$ | 20 μg/mL | 100 ± 8 | 90 ± 5 |
| $HgCl_2$ | 20 μg/mL | 90 ± 4 | 80 ± 9 |
| $PtCl_2$ | 20 μg/mL | 94 ± 6 | 70 ± 3 |
| $CuCl_2$ | 20 μg/mL | 100 ± 3 | 80 ± 7 |
| Control[b] | | <6 | <6 |

[a] Mean ± SD.
[b] No Pseudomonas added

EXAMPLE 6

Treatment of Organometallic Contaminants

Cultures of *Pseudomonas maltophila* ATCC 53510 are grown in the presence of methyl mercury, tetraethyl lead or tributyl tin for 48 h at 32° C. without aeration. Two-ml aliquots of the resulting mixture are filtered or placed on a sucrose gradient. The following metals (as % of amount added) are found on the filter or in the 50% layer of the sucrose gradient, respectively: Hg, 66%, 48%; Pb, 45%, 39% and Sn 38%, 44%. In control experiments, 90–100% of the metals are recovered in the filtrate or in the top layer of the sucrose gradient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of this invention to adapt it to various usages and conditions.

We claim:

1. A process for reducing the concentration of ionic species of at least one heavy metal from the group consisting of $Pb^{++}$, $Au^+$, $Ag^+$, $SeO_3^=$, $Pt^{++}$, and $Cu^{++}$ in an aqueous waste solution by conversion to one or more corresponding elemental metals, comprising contacting the aqueous waste solution containing ionic species of at least one heavy metal with a culture of *Pseudomonas maltophila* ATCC 53510 in the presence of the an amount of nutrient medium sufficient to satisfy nutritional requirements of cells of the culture of *Pseudomonas maltophila* ATCC 53510.

2. The process of claim 1, wherein the aqueous waste solution is contacted with the culture of Pseudomonas organism at a temperature from about 5° to about 35° C.

3. The process of claim 1, wherein the aqueous waste solution is contacted with the culture of Pseudomonas organism at pH from about 6 to about 8.

4. The process of claim 1, wherein the aqueous waste solution is contacted with the culture of Pseudomonas under aerobic conditions.

5. The process of claim 1, wherein air is bubbled through a mixture of the aqueous waste solution and the culture of Pseudomonas organism.

6. The process of claim 1, wherein the aqueous waste solution is contacted with the culture of Pseudomonas in an essentially liquid medium, products from the thus-contacted liquid waste solution are filtered to separate a filtrate from a solid residue and at least one elemental metal is recovered from the thus-separated solid residue.

7. The process of claim 1, wherein the aqueous waste solution is contacted with a culture of Pseudomonas affixed to a support.

8. the process of claim 1, carried out as a batch process in the presence of at least $10^8$ Pseudomonas cells/ml of solution being treated and wherein air is bubbled into a mixture of aqueous waste solution and culture.

9. The process of claim 1, carried out as a continuous process in the presence of at least $10^4$ Pseudomonas cells/ml of solution being treated and wherein air is bubbled into a mixture of aqueous waste solution and culture.

* * * * *